United States Patent [19]

Mikkelsen

[11] Patent Number: Plant 5,253

[45] Date of Patent: Jul. 3, 1984

[54] KALANCHOE PLANT NAMED ETERNITY

[75] Inventor: James C. Mikkelsen, Ashtabula, Ohio

[73] Assignee: Mikkelsens, Inc., Ashtabula, Ohio

[21] Appl. No.: 422,523

[22] Filed: Sep. 23, 1982

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A kalanchoe cultivar named Eternity particularly characterized by the development of the total salmon red inflorescence without deterioration of the initial flowering of the terminal florets, excellent compact self branching growth with dark green crenate foliage, enhancing the potential of production of kalanchoe hanging baskets.

1 Drawing Figure

The present invention relates to a new and distinct cultivar of kalanchoe plant, botanically known as kalanchoe, and referred to by the cultivar name Eternity. Eternity was developed by me through controlled breeding by crossing seedling 78-874-5 (seed parent) × seedling #78-890-4 (pollen parent). Asexual reproduction by stem cuttings has shown that the unique features of this new kalanchoe are stabilized and are reproduced true to type in successive propagations.

The following characteristics distinguish the new kalanchoe from both its parent cultivars and other cultivated kalanchoes of this type known and used in the floriculture industry:

1. There is no known commercial cultivar that can be directly compared to Eternity because of its many unique qualities.

2. The flower color is a distinct reddish salmon shade with a very slight blue overtone in the central area of the petals.

3. The florets mature over an extremely long period of up to 6–8 weeks without deterioration. The flower color will fade uniformly in the inflorescence to a pleasing light salmon and remain that way without petal breakdown for another 6–8 weeks. Thus the keeping qualities surpass any present cultivar by two or three times.

4. This remarkable keeping quality allows the greatest latitude for sales. Also, the ultimate consumer will receive the utmost satisfaction of this long flowering characteristic.

5. Nearly 100% of the florets will open and remain intact with uniform coloration.

6. The self branching characteristic is more pronounced than in any other commercial kalanchoe having the same vigorous growth habits. The main stem, laterals, peduncles, and pedicels are strong, vigorous, but not crude or rough in appearance.

7. The total number of cymes developing in the total inflorescence is remarkably high, often developing flowering to the basal nodes.

8. The combined qualities of growth and flowering opens a new development of flowering hanging baskets for year round production. Flowering trials outside at Ashtabula, Ohio in 1982 indicate a flowering basket could be expected to flower for 16 weeks in a slightly sheltered area.

9. Flowering 10 cm. pots have produced up to 600 or more florets in flower at one time, and without signs of deterioration until the total inflorescence is in flower.

10. 10 cm. pots placed in a well lighted south window have flowered in local homes and maintained a pleasing and respectable flowering display for 3 months. Several trials went to 4 months.

11. The foliage is clean, well formed and has a distinct appearance with crenated to sinuated leaf margins. Leaves and flowers are symmetrical around the axis of the plant.

12. Foliage is highly resistant to powdery mildew.

13. The new cultivar is quite responsive to changes in the amount of light energy, flowering in as little as 8 weeks in the summer and taking up to 16 weeks in the winter. This unfavorable quality is more than offset by the long lasting flowering habit.

The accompanying colored photograph taken in May 1982 illustrates in perspective view the overall appearance of Eternity grown in a 10 cm. plastic pot, and showing the colors as true as it is reasonably possible to obtain in a colored reproduction of this type.

The following is a detailed description of my new kalanchoe cultivar based on plants produced under commercial practices in the greenhouses of Mikkelsens, Inc., Ashtabula, Ohio. Color references are made to The Royal Horticultural Society Colour Chart except where general terms of ordinary dictionary significance are used.

PARENTAGE

A controlled cross of my kalanchoe seedling 78-874-5 as a seed parent with seedling 78-890-4 as a pollen parent.

PROPAGATION (A) Type cutting: Tip or stem cutting.

(B) Time to root: 10–12 Days at 21° C. night temperature summer, 15–18 at 21° C. night temperature winter.

(C) Rooting habit: Fibrous, dendritic, abundant.

PLANT DESCRIPTION (A) Form: Upright, short, compact, close internoded, full bushy succulent.

(B) Habit of growth: Normal growth rate except in very low light environments, becoming slower in this environment than most commercial kalanchoes of this type; self branching.

(C) Foliage: Leaves simple, opposite, symmetrical and abundant; dark green with some twisting on lower mature foliage.

(1) *Size.*—When grown for production in 10 cm. pot, leaves are 6–7 cm. wide and 10–12 cm. long.

(2) *Shape.*—Obovate, apex obtuse, base acute, some twisting of lower, more mature leaves.

(3) *Texture.*—Glabrous, coriaceous, succulent.

(4) *Margin.*—From broadly crenate to sinuate.

(5) *Color.*—Young foliage top side, yellow green 147A, under side, yellow 148B–C. Mature foliage top side, as dark as green 139A, under side, yellow green 148B.

FLOWERING DESCRIPTION (A) Flowering habits: Inflorescence of each peduncle is formed by dichotomous branching, terminal florets blooming first followed by terminal florets of secondary peduncles. Total time to have all florets in flower is 6–8 weeks. The first flowers will be intact. The total inflorescence will continue to flower for another 6–8 weeks giving up to 12–16 weeks of complete flowering without obvious deteriation. As illustrated, many peduncles originate from stem nodes. If plants are given sufficient space, flowering has occurred at the basal nodes as well as the terminal nodes.

(B) Natural flowering season: Mid to late January. Flowering time under controlled day length at 20° C. night temperature in summer is 8–9 weeks; in winter, 15–16 weeks. Although somewhat slow to flower, the long shelf life allows grower to distribute over long period of time.

(C) Flower buds: Symmetrically round and oblong, approximately 5–6 mm. long before opening, then becoming tubular and sheathed within four sepals.

(D) Flowers borne: Compound dichasial cyme on strong peduncles; individual florets on 6 mm. long pedicels.

(E) Quantity of flowers: Because of the extremely long keeping qualities of each floret, the floral appearance at maturity of the inflorescence shows an unusual high flower count. Also the actual number of cymes originating from the stem is unusually high.

(F) Petals:

(1) *Shape.*—Slightly oval, apex cuspidate.

(2) *Color.*—Top side when opening, red 43D-41D with slight blue tone; the whole inflorescence will fade to orange-red 32-C in 10 weeks without any floret deterioration; under side, red 48C–D.

(3) *Number of petals.*—Generally 4 but occasionally 5.

(G) Reproductive organs:

(1) *Stamens.*—Number, 2 pairs of 4; quite often 2 from below will be at top with stigma with other 4. (a) Anther shape: Flat, oval, color yellow. (b) Filament color: Translucent green. (c) Pollen color: Yellow.

(2) *Pistels.*—(a) Stigma shape: Irregularly round, flat crystalline top, color cream. (b) Style color: Light green. (c) Ovaries: 4, Celled, size 5 mm., color light green.

DISEASE RESISTANCE

Extremely resistant to botrytis petal blight and powdery mildew.

I claim:

1. A new and distinct cultivar of kalanchoe known by the cultivar name Eternity, as described and illustrated, and particularly characterized by its salmon red flower color; massive inflorescence without deterioration of the initial flowering of the terminal florets, and its excellent compact self branching growth with dark green crenate foliage, thereby increasing the potential of production of kalanchoe hanging baskets.

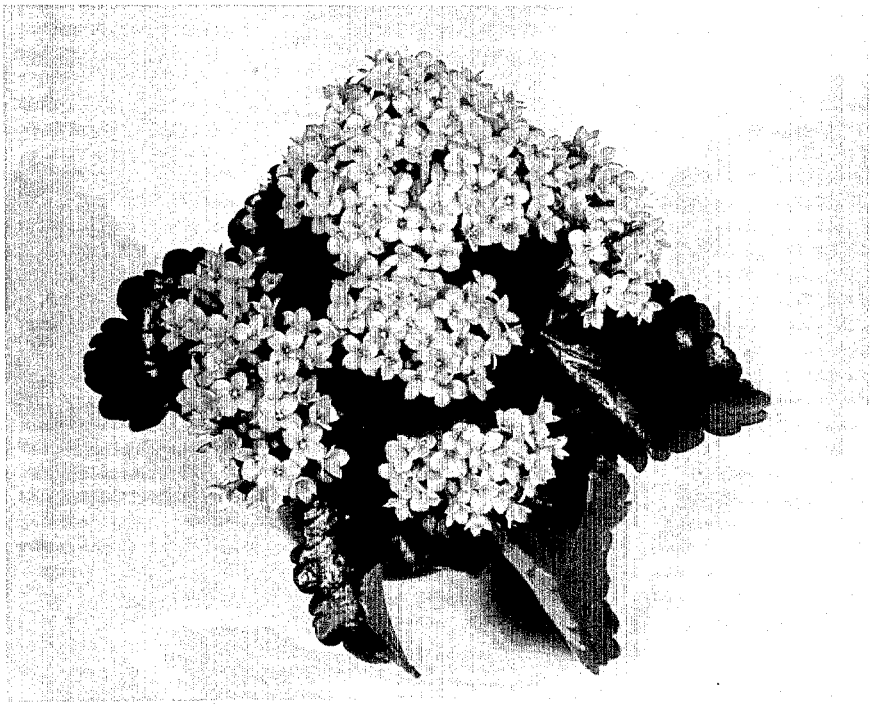

* * * * *